(12) United States Patent
Harris

(10) Patent No.: US 8,048,006 B2
(45) Date of Patent: Nov. 1, 2011

(54) ULTRASOUND THERAPY

(75) Inventor: Susan Jane Harris, York (GB)

(73) Assignee: Smith & Nephew PLC, London (GB)

( * ) Notice: Subject to any disclaimer, the term of this patent is extended or adjusted under 35 U.S.C. 154(b) by 940 days.

(21) Appl. No.: 11/462,271

(22) Filed: Aug. 3, 2006

(65) Prior Publication Data

US 2007/0038098 A1   Feb. 15, 2007

(30) Foreign Application Priority Data

Aug. 12, 2005   (GB) .................................. 0516586.5

(51) Int. Cl.
  *A61H 1/00*   (2006.01)
(52) U.S. Cl. .......................................................... 601/2
(58) Field of Classification Search .................. 600/411, 600/439, 11; 601/2
See application file for complete search history.

(56) References Cited

U.S. PATENT DOCUMENTS

| | | | | |
|---|---|---|---|---|
| 4,341,762 A | * | 7/1982 | Haast | 424/184.1 |
| 4,530,360 A | * | 7/1985 | Duarte | 607/51 |
| 5,413,550 A | * | 5/1995 | Castel | 601/2 |
| 5,520,612 A | * | 5/1996 | Winder et al. | 601/2 |
| 7,410,469 B1 | * | 8/2008 | Talish et al. | 601/2 |
| 7,510,536 B2 | * | 3/2009 | Foley et al. | 601/2 |
| 2003/0225331 A1 | * | 12/2003 | Diederich et al. | 600/437 |
| 2006/0134109 A1 | * | 6/2006 | Gaitanaris et al. | 424/143.1 |
| 2006/0241522 A1 | * | 10/2006 | Chandraratna | 601/2 |

FOREIGN PATENT DOCUMENTS

WO   WO2004040000 A2   5/2004

OTHER PUBLICATIONS

Office Action issued in Australian Patent Application No. 2006203281 dated Jul. 30, 2010, 3 pages.

\* cited by examiner

*Primary Examiner* — Tse Chen
*Assistant Examiner* — Elmer Chao
(74) *Attorney, Agent, or Firm* — Fish & Richardson P.C.

(57) ABSTRACT

A method of treating a peripheral neuropathy, peripheral neurodegenerative disease, or peripheral nerve trauma is disclosed. The method includes the step of applying an ultrasound signal to an anatomical location on a patient.

9 Claims, 3 Drawing Sheets

ULTRASOUND THERAPY

This application claims the benefit of U.K. Provisional Application 0516586.5, filed Aug. 12, 2005 titled "Ultrasound Therapy for Diabetic Peripheral Neuropathy" and the entire contents of which is hereby incorporated by reference.

TECHNICAL FIELD OF THE INVENTION

This invention is related to the area of disorders of the nervous system. In particular it relates to disorders of the peripheral nervous system and the use of ultrasound as a method of treating a peripheral neuropathy, peripheral neurodegenerative disease or peripheral nerve trauma.

BACKGROUND OF THE INVENTION

Peripheral neuropathy is a failure of the nerves that carry information to and from the brain and spinal cord. This produces pain, loss of sensation, and inability to control muscles.

In some cases, the failure of nerves that control blood vessels, intestines, and other organs results in abnormal blood pressure, digestion problems, and loss of other basic body processes. Peripheral neuropathy may involve damage to a single nerve or nerve group (mononeuropathy) or may affect multiple nerves (polyneuropathy).

There are numerous reasons for nerves to malfunction. In some cases, no cause can be identified. Damage to nerves can result from one of the specific conditions associated with neuropathy, including: (1) Hereditary disorders, such as Charcot-Marie-Tooth disease or Friedreich's ataxia; (2) Systemic or metabolic disorders, such as Diabetes (diabetic neuropathy), Dietary deficiencies (especially vitamin B-12), Excessive alcohol use (alcoholic neuropathy), Uremia (from kidney failure), or Cancer; (3) Infectious or inflammatory conditions, such as AIDS, Hepatitis, Colorado tick fever, diphtheria, Guillain-Barre syndrome, HIV infection without development of AIDS, leprosy, Lyme, polyarteritis nodosa, rheumatoid arthritis, sarcoidosis, Sjogren syndrome, syphilis, systemic lupus erythematosus, or Amyloid; (4) Exposure to toxic compounds, such as sniffing glue or other toxic compounds, nitrous oxide, industrial agents—especially solvents, heavy metals (lead, arsenic, mercury, etc.), or drugs; and (5) Miscellaneous causes, such as ischemia (decreased oxygen/decreased blood flow), or prolonged exposure to cold temperature.

Diabetic neuropathy is a nerve disorder caused by diabetes. Symptoms of neuropathy include numbness and sometimes pain in the hands, feet or legs. Nerve damage caused by diabetes can also lead to problems with internal organs such as the digestive tract, heart and sexual organs, causing indigestion, diarrhea or constipation, dizziness, bladder infections and impotence.

The cause of diabetic neuropathy remains undefined, but several factors are likely to contribute to the disorder. For example, high blood glucose causes chemical changes in the nerves that impair the nerves' ability to transmit signals.

Diabetic neuropathy can affect virtually every part of the body. Diffuse (peripheral) neuropathy affect the legs, feet, arms and hands. Diffuse (autonomic) neuropathy affects the heart, digestive system, sexual organs, urinary tract and sweat glands. Focal neuropathy affects the eyes, facial muscles, hearing, pelvis and lower back, thighs and abdomen.

Diabetic individuals are also prone to developing compression neuropathies. The most common form of compression neuropathy is carpal tunnel syndrome. Asymptomatic carpal tunnel syndrome occurs in 20-30% of diabetes sufferers whilst symptomatic carpal tunnel syndrome occurs in 6-11%. Numbness and tingling of the hand are the most common symptoms. Diabetic peripheral neuropathy is also a fundamental cause of a large proportion of diabetic foot ulcers. The lack of sensation caused by this condition results in the individual being unable to detect points of pressure that would normally cause low level pain and therefore behavior would be corrected to stop the pain (i.e., relieve pressure on that part of the foot). Without that sensation the insult continues and results in ulceration of the skin that can then become a chronic wound and in a significant number of cases results in amputation.

Other examples of neuropathies include chemotherapy-induced neuropathy, alcoholic neuropathy and HIV/AIDS neuropathy.

Regaining the sensation by stimulating nerve regeneration would therefore have a significant impact on the quality of life of those individuals suffering from peripheral neuropathy, particularly diabetic peripheral neuropathy.

The current goals of treating diabetic neuropathy are to prevent progression and reduce the symptoms of the disease. Tight control of glucose is important to prevent progression. To reduce the symptoms, topical treatment with Capsaicin or oral medication like amitriptyline, gabapentin, and carbamazepine have been used successfully. Analgesics (pain medications) may work for some patients on a short-term basis. But, in most cases, they usually do not provide much benefit.

The current protocols for treatment of neuropathies are limited to relieving pain and discomfort, as well as to preventing additional tissue damage. Therefore, there is a need in the art for a therapy which promotes nerve regeneration rather than treating the symptoms of the pathologies.

SUMMARY OF THE INVENTION

It is in view of the above problems that the present invention was developed. The invention is a method of treating a peripheral neuropathy, peripheral neurodegenerative disease, or peripheral nerve trauma comprising the step of applying an ultrasound signal to an anatomical location on a patient. The peripheral neuropathy, peripheral neurodegenerative disease, or peripheral nerve trauma may include one or more of the following: a systemic or metabolic neuropathy, such as diabetic neuropathy, uremic neuropathy, alcoholic neuropathy, a neuropathy caused by dietary deficiencies (especially vitamin B-12) or a neuropathy caused by cancer; a toxic neuropathy, such as chemotherapy-induced neuropathy or anti-retroviral drug-induced neuropathy; a peripheral neuropathy, peripheral neurodegenerative disease, or peripheral nerve trauma associated with AIDS, hepatitis, Colorado tick fever, diphtheria, syphilis, Lymes' disease or leprosy; a peripheral neuropathy, peripheral neurodegenerative disease, or peripheral nerve trauma associated with polyarteritis nodosa, rheumatoid arthritis, sarcoidosis, Sjorgen syndrome or systemic lupus erythematosus; a motor neuron disease such as amyotrophic lateral sclerosis, spinobulbar muscular atrophy or spinal muscular atrophy; a hereditary disease, such as Charcoat-Marie-Tooth disease; a peripheral neuropathy, peripheral neurodegenerative disease, or peripheral nerve trauma caused by exposure to toxic compounds, such as glue, nitrous oxide, industrial agents (such as solvents) or heavy metals (such as lead, arsenic or mercury); a peripheral neuropathy, peripheral neurodegenerative disease, or peripheral nerve trauma caused by injury, ischeamia, or by prolonged exposure to cold temperatures; or where the peripheral neuropathy, peripheral neurodegenerative disease, or peripheral nerve trauma is idiopathic.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
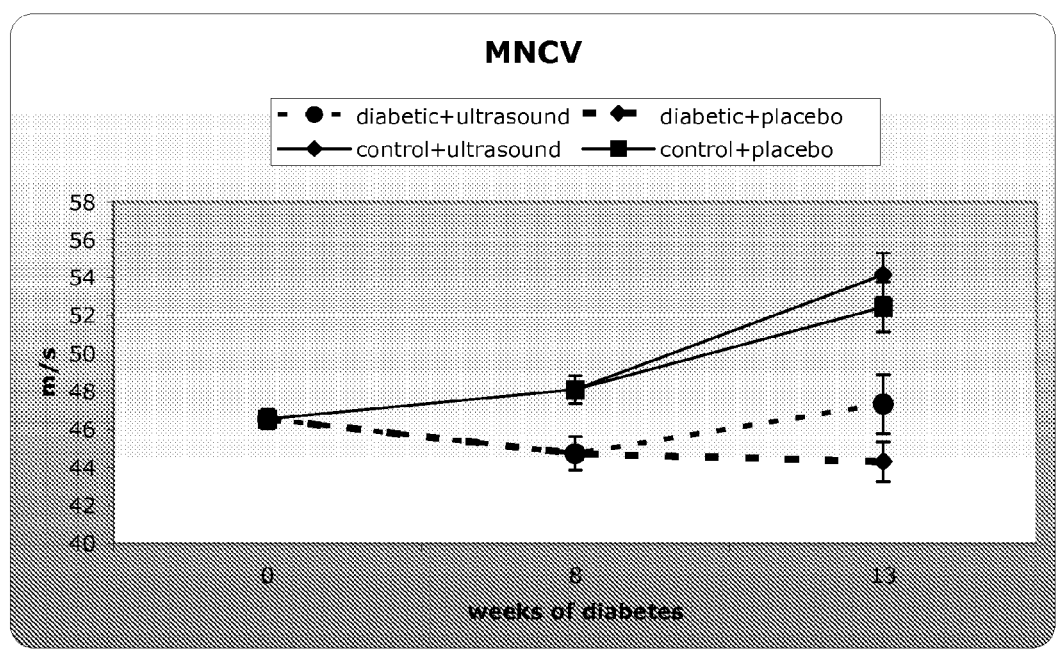
FIG. 1 illustrates left sciatic MNCV during the 12-week study, with ultrasound or placebo treatment for weeks 9-12. Data are group mean±SEM

Nerve conduction velocity (NCV) is a test of the speed of conduction of impulses through a nerve. NCV is related to the diameter of the nerve and the normal degree of myelination (the presence of a myelin sheath on the axon) of the nerve.

The test is used to diagnose nerve damage or destruction. The nerve is stimulated, usually with surface electrodes, which are patch-like electrodes (similar to those used for ECG) placed on the skin over the nerve at various locations. One electrode stimulates the nerve with a very mild electrical impulse. The resulting electrical activity is recorded by the other electrodes. The distance between electrodes and the time it takes for electrical impulses to travel between electrodes are used to calculate the nerve conduction velocity.

The nerve conduction study comprises the following two components: Motor nerve conduction velocity and Sensory nerve conduction velocity. Motor nerve conduction velocity (MNCV) is performed by electrical stimulation of a peripheral nerve and recording from a muscle supplied by this nerve. By stimulating in two or more different locations along the nerve, the NCV in different segments can be determined. Calculations are performed using the difference between the different stimulating electrodes and the difference in time of the response of the muscle to stimulation.

Sensory nerve conduction velocity (SNCV) is performed by electrical stimulation of a peripheral nerve and recording from a purely sensory portion of the nerve, such as on a finger. The SNCV is calculated from the time from stimulation to recording the action potential in the nerve and knowing the distance between the stimulating and recording electrodes.

The application of ultrasound to a neuropathic area results in a substantial increase in the MNCV measurement. This non-invasive technique of the invention involves placing an applicator on or adjacent to the skin of the patient, with an ultrasound transducer directing sound waves through the neuropathic area.

One of the advantages of the method is that it utilizes non invasive ultrasound technology. The transducer is applied to the skin of the patient, directly over the neuropathic site, with the use of a coupling gel (for example, of the same types of coupling gels used in ultrasound diagnostic applications). The electronic circuitry for energizing the transducer consists of conventional circuits, such as radio frequency oscillator and a pulse generator.

The ultrasound signal may be, for example, a pulsed radio frequency ultrasound signal.

The pulsed radio frequency ultrasound signal has a frequency in the range of 1.3-2 MHz. The energy is applied in short pulses of bursts; the width of each energy pulse or burst being in the range of 10-2,000 microseconds, and the burst or pulse repetition frequency is in the range of 100-1,000 Hz.

The pulsed radio frequency ultrasound signal may be applied daily, with the duration of treatment being in the range of 1-55 minutes, although the preferred range is about 10 to about 30 minutes. It is important that the ultrasound power be kept below a safety threshold so that the skin is not damaged.

In some embodiments, the power intensity of the ultrasound signal is no higher than 100 milliwatts per square centimeter.

The invention includes the method of treating a peripheral neuropathy, peripheral neurodegenerative disease, or peripheral nerve trauma. The method includes the step of applying an ultrasound signal to an anatomical location on a patient. The method may include the step of pulsing a radio frequency ultrasound signal at a frequency in the range of about 1.3 to about 2 MHz. The method may include the step of pulsing a radio frequency ultrasound signal at a frequency in the range of about 100 to about 1,000 Hz. The method may include the step of pulsing a radio frequency ultrasound signal for a duration in the range of about 10 to about 2,000 microseconds. The method may include the step of transmitting an ultrasound signal at an intensity no higher than about 100 milliwatts per square centimeter. The method may include the step of applying the ultrasound signal daily to the peripheral neuropathy, peripheral neurodegenerative disease, or peripheral nerve trauma. The method may include the step of applying the ultrasound signal to the peripheral neuropathy, peripheral neurodegenerative disease, or peripheral nerve trauma for between 10 and 30 minutes per day.

The use of ultrasound for treating a peripheral neuropathy, peripheral neurodegenerative disease, or peripheral nerve trauma can be illustrated in greater detail by the following example. However, it should be understood that the invention is not limited to this example.

Example I

Introduction

The study was designed to determine whether established degenerative neuropathy in rats that presents after 8-12 weeks of hyperglycemia can be reversed by ultrasound treatment. Insulin-deficient diabetes was induced into female rats. Rats were placed in a restraint tube, and the animals were subjected to an ultrasound treatment for 20 minutes per day, 5 days per week during weeks 9-12 of diabetes. Ultrasound treatment resulted in an improvement in MNCV.

All procedures described herein have been published in the following references: (1) Mizisin A P, Vu Y, Shuff M, Calcutt N A. (2004), Ciliary Neurotrophic Factor Improves Nerve Conduction And Ameliorates Regeneration Deficits In Diabetic Rats. Diabetes 53:1807-1812; (2) Calcutt N A, Allendoerfer K L, Mizisin A P, Middlemas A, Freshwater J D, Burgers M, Ranciato R, Delcroix J D, Taylor F R, Shapiro R, Strauch K, Dudek H, Engber, T M, Galdes A, Rubin L L, Tomlinson D R. (2003), Therapeutic Efficacy Of Sonic Hedgehog Protein In Experimental Diabetic Neuropathy. J Clin Invest. 111:507-514; (3) Calcutt N A. (2004), Modeling Diabetic Sensory Neuropathy In Rats. Methods Mol Med. 99:55-65; and (4) Malmberg A B, Mizisin A P, Calcutt N A, von Stein T, Robbins W R, Bley K R. (2004), Reduced Heat Sensitivity And Epidermal Nerve Fiber Immunostaining Following Single Applications Of A High-Concentration Capsaicin Patch. Pain 111:360-367. Each reference is incorporated by reference in its entirety.

Methods

The animal characteristics are provided in Table 1:

TABLE 1

| Animals | |
|---|---|
| SPECIES | Rat (female) |
| STRAIN | Sprague-Dawley |
| SOURCE | Harlan Sprague Dawley, Inc., Indianapolis, Indiana |
| WEIGHT | 250-275 grams (adult) |
| HUSBANDRY | Room temperature was maintained between 65 to 82° F. with relative humidity between 30 to 70%. The room was illuminated with fluorescent lighting on a daily 12-hour light/dark cycle. All animals had free access to dry food and municipal water. Cages were cleaned daily. |

The rats were grouped as shown in Table 2.

TABLE 2

| GROUPS (10 RATS/GROUP): | Control and placebo treatment |
|---|---|
| | Control and ultrasound treatment |
| | Stz-diabetic and placebo treatment |
| | Stz-diabetic and ultrasound treatment |

Insulin-deficient diabetes was induced by a single intraperitoneal injection of streptozotocin (50 mg/kg in sterile saline) to ablate pancreatic β cells. Hyperglycemia was confirmed by assay of blood samples taken 3 days after streptozotocin injection and at the conclusion of the study. Rats displaying marked weight loss (25% starting weight) or sedated behavior to audiovisual stimuli received 2 U insulin thrice weekly. All rats were inspected daily.

Ultrasound test devices were supplied by Smith & Nephew, Plc. The application protocol was 20 minutes treatment per day, ultrasound frequency of 1.5 MHz pulsed at 1 kHz and 30 mW/cm2 intensity (SATA), with a pulse width of 200 μs.

Rats were placed in a restraint tube and the ultrasound probe placed in direct contact with the shaved flank of the left hind limb. Animals were treated for 20 minutes per day, 5 days per week during weeks 9-12 of diabetes with either an active or placebo device which was color coded (blue=active, black=placebo) so that the investigators were not aware of the treatment group until after all data had been collected.

Physiology and behavior measurements were made at least 24 hours after the last treatment. The physiology and behavior measurements are indicated in Table 3.

TABLE 3

| Onset of hyperglycemia | Midpoint of study (8 weeks) | End of study (12 weeks) |
|---|---|---|
| Body weight | Body weight | Body weight |
| Blood glucose | Blood glucose | Blood glucose |
| MNCV/SNCV | MNCV/SNCV | MNCV/SNCV |
| | Thermal response latency | Thermal response latency |
| | Tactile response threshold | Tactile response threshold |
| | | Nerve blood flow |
| | | Nerve light microscopy* |
| | | Footpad epidermal nerves** |

Table 3 notes:
*Mid-thigh sciatic nerve segments were immersion fixed for preparation as plastic sections for light microscopic and morphometric analysis of myelinated fiber axonal area.
**Skin from the plantar surface of the hind paw was immersion fixed for preparation as paraffin sections for light microscopic analysis of epidermal PGP 9.5 +ve fiber density (C fibers).

Results

Findings After 8 Weeks of Diabetes (Prior to Onset of Treatment)

Data are presented as cohort means for the 20 control rats and 21 diabetic rats prior to sub-division into the placebo or ultrasound arms of each cohort.

Diabetic rats showed the expected hyperglycemia and weight loss compared to control rats.

Figure 2:
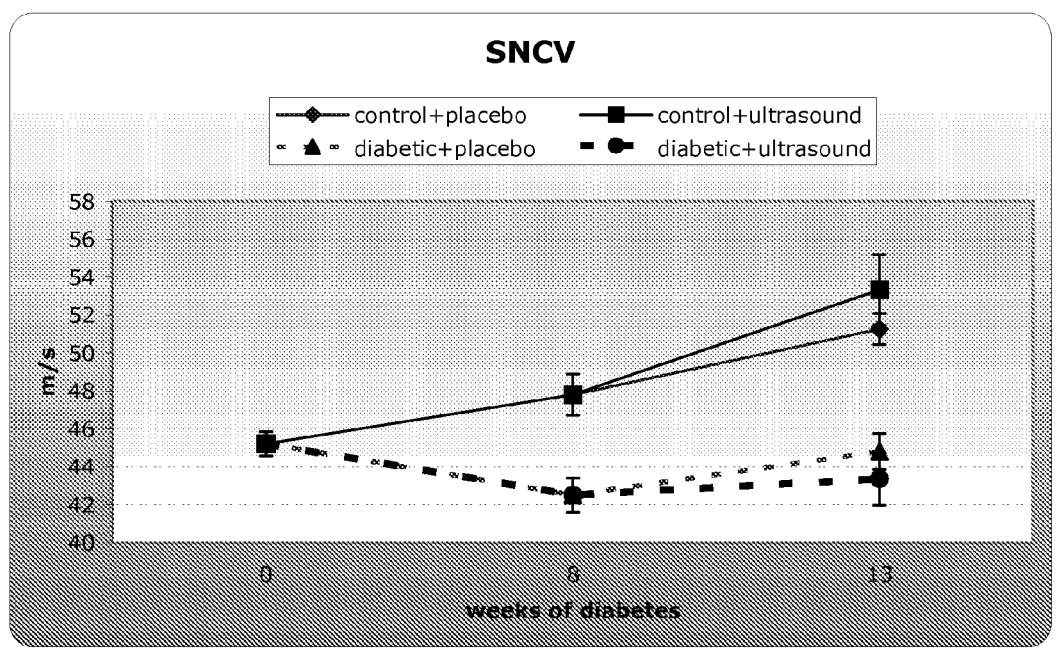
FIG. 2 illustrates left sciatic SNCV during the 12-week study, with ultrasound or placebo treatment for weeks 9-12. Data are group mean±SEM
Figure 3:
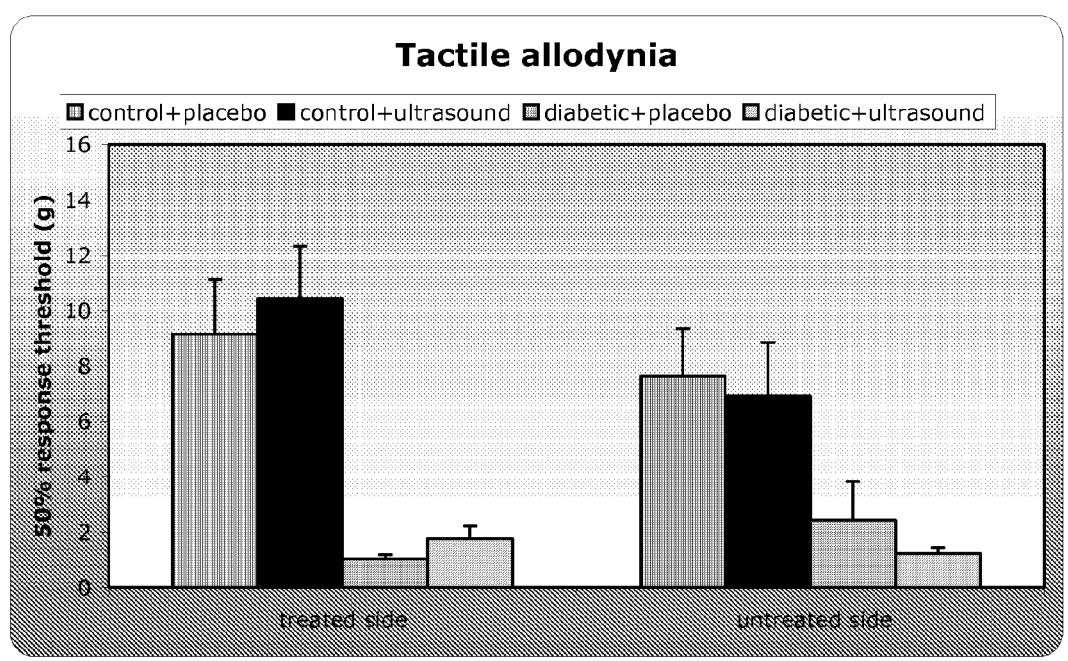
FIG. 3 illustrates tactile responses in the hind paw of both the untreated and treated limbs of control and diabetic rats after 12 weeks of hyperglycemia. Data are group mean+SEM.

Evidence of nerve dysfunction was indicated by slowing of both MNCV and SNCV in the left sciatic nerve (see FIGS. 1 & 2) and the presence of tactile allodynia at the plantar surface of both hind paws.

Findings at Week 12 of Diabetes (After 4 Weeks of Treatment)

Diabetic rats showed the expected hyperglycemia, weight loss and mild hypotension compared to control rats. Five diabetic rats received basal insulin treatment during the study as body weight dropped below 200 g. Of these, four had recovered weight and all five remained hyperglycemic at the end of the study. Ultrasound treatment was without effect in either group.

Control rats showed a time-dependent increase in sciatic MNCV and SNCV over the 12-week study period (see FIG. 1), indicating that the nervous system of these animals was still maturing. Ultrasound treatment for the last 4 weeks of the study was without marked effect in control rats.

Placebo-treated-diabetic rats showed a decrease in sciatic MNCV and SNCV over the 12-week study period. MNCV slowing after 12 weeks of hyperglycemia in rats has been attributed to a combination of metabolic (ischemia, oxidative stress) and structural (axonal atrophy) mechanisms. Ultrasound treatment begun on week 9 halted the progressive decline in MNCV and resulted in an improvement in MNCV.

CONCLUSIONS

Ultrasound therapy is effective in treating certain types of neuropathy.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The invention claimed is:

1. A method of treating a peripheral neuropathy or peripheral neurodegenerative disease, comprising:
    placing an ultrasound applicator adjacent to a patient's skin surface proximate a neuropathic area affected by the peripheral neuropathy or the neurodegenerative disease such that, during operation, the ultrasound applicator directs ultrasound through the neuropathic area; and
    applying ultrasound through the neuropathic area using the ultrasound applicator,
    wherein the ultrasound comprises a pulsed radio frequency ultrasound signal having a frequency in the range of 1.3 MHz to 2 MHz, consisting of pulses generated at a rate in the range of 100 Hz to 1,000 Hz with each pulse having a duration in the range of 10 microseconds to 2,000 microseconds, and having a power intensity no higher than 100 milliwatts per square centimeter, and
    wherein the peripheral neuropathy or peripheral neurodegenerative disease is selected from a group consisting of: a systemic or metabolic neuropathy, a toxic neuropathy, a motor neuron disease, a neuropathy resulting from an infection, and an idiopathic neuropathy.

2. A method according to claim 1, wherein the peripheral neuropathy or peripheral neurodegenerative disease is a systemic or metabolic neuropathy.

3. A method according to claim 2, wherein the metabolic neuropathy is a diabetic neuropathy.

4. A method according to claim 1, wherein the peripheral neuropathy or peripheral neurodegenerative disease is a toxic neuropathy.

5. A method according to claim 4, wherein the toxic neuropathy is anti-retroviral drug-induced neuropathy.

6. A method according to claim 1, wherein the peripheral neuropathy or peripheral neurodegenerative disease is a motor neuron disease.

7. A method according to claim 1, wherein the peripheral neuropathy or peripheral neurodegenerative disease results from an infection.

8. A method according to claim 1, wherein the peripheral neuropathy or peripheral neurodegenerative disease is idiopathic.

9. A method of treating a peripheral neuropathy or peripheral neurodegenerative disease, comprising:
    placing an ultrasound transducer proximate a neuropathic area selected for treatment; and
    operating the ultrasound transducer once per day and for a duration in the range of about 10 minutes to about 30 minutes to apply a pulsed radio frequency ultrasound signal to the neuropathic area to treat the peripheral neuropathy or peripheral neurodegenerative disease,
    the pulsed radio frequency ultrasound having a frequency in the range of 1.3 MHz to 2 MHz, consisting of pulses generated at a rate in the range of 100 Hz to 1,000 Hz with each pulse having a duration in the range of 10 microseconds to 2,000 microseconds, and having a power intensity no higher than 100 milliwatts per square centimeter, and
    the peripheral neuropathy or peripheral neurodegenerative disease being selected from a group consisting of: a systemic or metabolic neuropathy, a toxic neuropathy, a motor neuron disease, a neuropathy resulting from an infection, and an idiopathic neuropathy.

* * * * *